US009795499B2

(12) United States Patent
Ponce

(10) Patent No.: US 9,795,499 B2
(45) Date of Patent: Oct. 24, 2017

(54) APPARATUS HAVING BRACE ASSEMBLY FOR MUSCLE

(71) Applicant: Corpus Sanus, Toronto (CA)

(72) Inventor: Lester Ponce, Toronto (CA)

(73) Assignee: CORPUS SANUS, Toronto, Ontario (CA)

( * ) Notice: Subject to any disclaimer, the term of this patent is extended or adjusted under 35 U.S.C. 154(b) by 314 days.

(21) Appl. No.: 14/518,067

(22) Filed: Oct. 20, 2014

(65) Prior Publication Data

US 2015/0119781 A1    Apr. 30, 2015

Related U.S. Application Data

(60) Provisional application No. 61/895,150, filed on Oct. 24, 2013.

(51) Int. Cl.
*A61F 5/01* (2006.01)
*A61H 1/02* (2006.01)
*A63B 21/00* (2006.01)
*A63B 21/02* (2006.01)

(52) U.S. Cl.
CPC .......... *A61F 5/0127* (2013.01); *A61F 5/0111* (2013.01); *A61H 1/0237* (2013.01); *A63B 21/02* (2013.01); *A63B 21/4011* (2015.10)

(58) Field of Classification Search
CPC .. A61F 5/00; A61F 5/01; A61F 5/0102; A61F 5/0104; A61F 5/0111; A61F 5/0113; A61F 5/0127; A63B 21/02; A63B 21/065; A63B 21/40; A63B 21/4001; A63B 21/4011; A63B 21/4013; A63B 21/4015; A63B 21/4025; A63B 71/08; A63B 71/12; A63B 71/1225; A63B 2071/1266; A63B 2071/1275; A61H 1/0237; A61H 1/0262; A61H 1/0266
USPC ..... 602/23, 27–29; 601/27, 33, 34; 482/121, 482/122, 124, 131, 139
See application file for complete search history.

(56) References Cited

U.S. PATENT DOCUMENTS

| | | | |
|---|---|---|---|
| 2,116,445 A | | 5/1938 | Moore |
| 4,294,238 A | * | 10/1981 | Woodford ............. A61F 5/0111 2/22 |
| 4,844,058 A | | 7/1989 | Vogelbach |
| 5,833,640 A | | 11/1998 | Vazquez, Jr. et al. |
| 5,843,010 A | * | 12/1998 | Bodmer ................ A61F 5/0111 128/882 |
| 6,617,485 B2 | | 9/2003 | Herzberg |
| 6,840,894 B2 | | 1/2005 | Lerner |
| 6,945,947 B2 | | 9/2005 | Ingimundarson et al. |
| 7,153,246 B2 | | 12/2006 | Koscielny et al. |
| 7,354,413 B2 | * | 4/2008 | Fisher .................. A61F 5/0113 602/23 |
| 7,491,186 B2 | | 2/2009 | Zeide et al. |

(Continued)

*Primary Examiner* — Keri J Nelson

(57) ABSTRACT

An apparatus includes a brace assembly and a force-application assembly. The brace assembly includes a muscle-origin portion configured to connect proximate to a muscle origin of a muscle. The brace assembly also includes a muscle-insertion portion configured to connect proximate to a muscle insertion of the muscle. The force-application assembly is configured to connect to the muscle-origin portion and the muscle-insertion portion. The force-application assembly is also configured to extend between the muscle-origin portion and the muscle-insertion portion once coupled to do just so.

15 Claims, 10 Drawing Sheets

(56) References Cited

U.S. PATENT DOCUMENTS

| | | |
|---|---|---|
| 7,935,067 B2 * | 5/2011 | McChesney .......... A61F 5/0111 602/23 |
| 8,007,457 B2 | 8/2011 | Taylor |
| 2012/0010548 A1 | 1/2012 | Scholtes et al. |

* cited by examiner

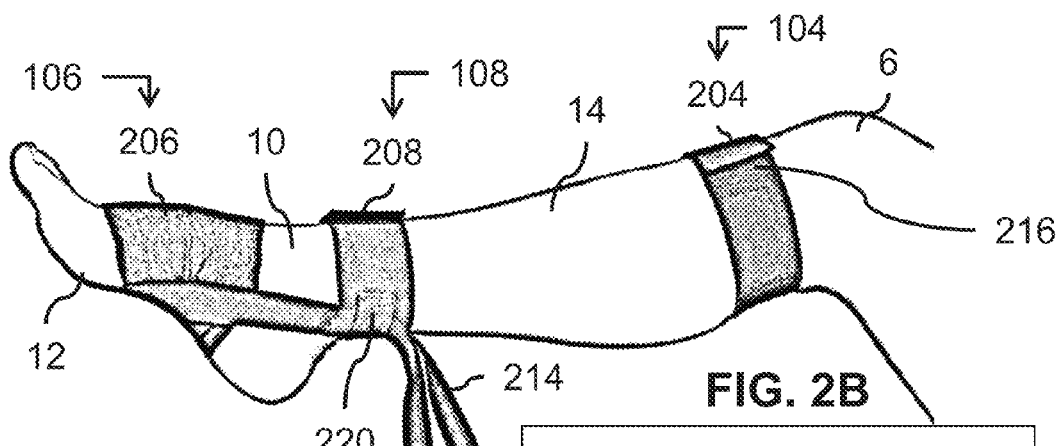
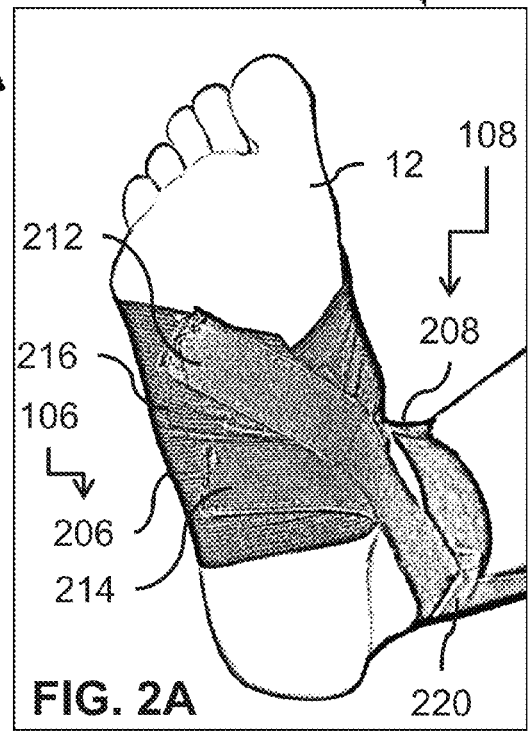
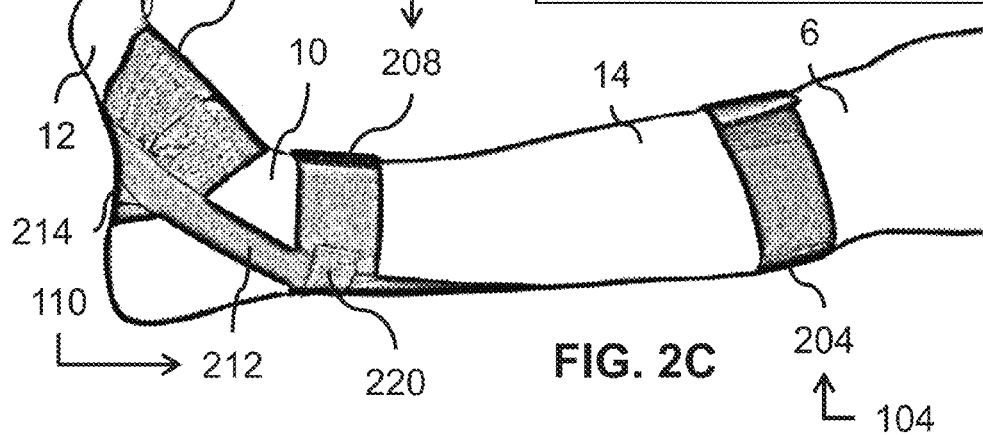

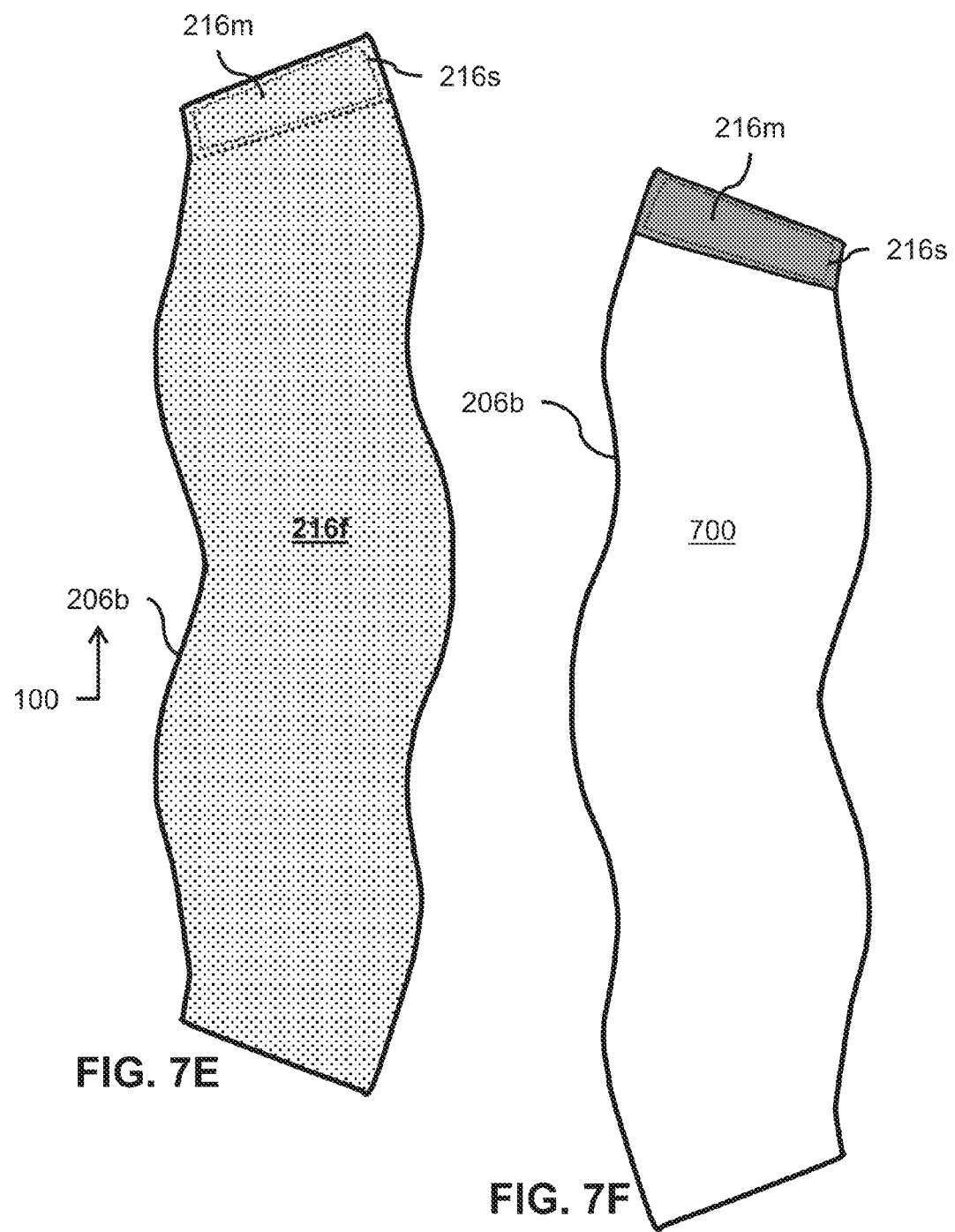

APPARATUS HAVING BRACE ASSEMBLY FOR MUSCLE

CROSS-REFERENCE TO RELATED PATENT APPLICATION(S)

This application claims the benefit and the priority date of prior U.S. Provisional Application No. 61/895,150, filed Oct. 24, 2013, entitled APPARATUS HAVING BRACE ASSEMBLY FOR MUSCLE, and which is incorporated herein by reference. This application is related to and claims domestic priority benefits under 35 USC §119(e) from U.S. Provisional Patent Application Ser. No. 61/895,150, filed on Oct. 24, 2013, entitled APPARATUS HAVING BRACE ASSEMBLY FOR MUSCLE, the entire content of which is expressly and hereby incorporated hereinto by reference.

TECHNICAL FIELD

Some aspects are generally related to (and are not limited to) an apparatus, including a brace assembly for a muscle.

BACKGROUND

Generally, muscular function shuts down because of trauma and/or injury inflicted to the muscle, ligaments, joints and/or bones. For instance, the front and outside of the lower leg includes the shin, the top of the foot and the outside of the ankle up to the knee. It is home to the tibialis anterior, the tibialis posterior, the extensor digitorum, and the peroneal muscles. It is also a common area for overuse injuries in the form of tendonitis, muscle strains/sprains and spasms, the most popular of which is "shin splints."

In normal walking gait, these muscles are responsible for lowering the foot to the ground. The front muscles or dorsiflexors have a primary function to pull the toes and ankle upwardly, and to slowly lower the foot to the ground from heel to toe. The outer muscles have a primary function to evert the foot or tilt the foot out to the side away from the body, and to slowly lower the foot to the ground from the outside of the heel, over the arch and onto the big toe. The term "evert" means to turn a structure away from a normal position (such as, to turn the structure outward). As a person moves through push off, these muscles rely on elastic recoil to pull the toes and ankle up for clearance through the swing phase. This reduces a large amount of the stress on these muscles and allows them to use their full strength for shock absorption at heel strike. However, if push off is decreased in any way (as a result of over pronation, high arches, tight calves, for instance), these muscles must then work overtime to not only pull the toes/ankle upwardly so that the person does not trip over them and but also to slowly lower the foot to the ground upon heel strike. Over time, these muscles may become overworked and can break down and/or become deactivated (unable to actively contract when required to do just so).

The shin is the common name for the front of the lower leg bone (tibia) and its associated muscles and tendons. While muscles on the front of the leg (primarily the tibialis anterior) serve to point the toes and foot upwards (dorsiflexion), the tibialis posterior serves to point the toes and foot downwards (plantar flexion). Anterior shin splints exist on the front of the lower leg, while posterior shin splints present pain along the inside edge of the lower leg in the tibialis posterior tendon. The role of the tibialis posterior is to support the arch as the body moves over the foot during the gait cycle. In medical terms, posterior shin splints are known as posterior tibial tendon dysfunction, or PTTD. PTTD describes a weakening of the tibialis posterior tendon, and in severe cases may result in a rupture of the tendon. Posterior shin splints may be considered the onset of PTTD. If the forces (singular or cumulative) applied to the tendon are greater than what the tendon can bear in its current state, inflammation and micro-trauma will result. Excessive pronation, changes of shoe or running surface, compensations for previous injuries or poor mechanics, and general overuse are all common causes of posterior shin splints. Other causes include muscle imbalances in the leg, flat feet or fallen arches, and activity that may require frequent and abrupt changes in direction (which are symptoms of muscular dysfunction).

The posterior tibialis is often overlooked. It is a major source of shin splints and plantar fasciitis. Injury to the anterior tibialis is called a shin splint (also known as tibial-stress syndrome). The shin splint is a repetitive overuse injury caused by tight calves and ankles, improper footwear, or abnormal mechanics (i.e. running form or cycling form of a person). Posterior shin splint pain is specific to the medial ankle, just behind the medial malleolus and along the lower and inner shin. Note that this location is different from anterior shin splints. Pain (at an area) may be felt to the touch, and the area having the pain (generally) may not exhibit visible swelling. The pain can range anywhere from faint and annoying to sharp and debilitating. When the condition worsens, bumps can be felt along the area and represent major inflammation and distortions in the underlying fascia. At the onset, pain is generally felt at the beginning of activity and dissipates over a relatively short period of time. As the condition worsens, the pain is constant and may result in stress fractures.

SUMMARY

I, the inventor, have researched a problem associated with muscle function and dysfunction. After much study, I believe I have arrived at an understanding of the problem and its solution, which are stated below.

Generally, the inventor believes that problems associated with muscular dysfunction may be overcome by application of muscular activation, preferably during normal or typical physical actions of the user. For instance, some of the factors that cause the specific muscles identified above to lose their functionality are injuries, trauma, and sprain and strain on the ankle that may lead to fractures of the ankle Some additional factors may include arthritic changes (because of a chronic inflammatory process), and/or improper footwear that leads to trauma. In addition, some genetic (hereditary) factors may be involved that alter muscle functionality that leads to muscular dysfunction.

In order to mitigate, at least in part, the problems identified above, in accordance with another aspect of my work, I (the inventor) have developed an apparatus. The apparatus includes a brace assembly. The brace assembly includes a muscle-origin portion configured to connect proximate to a muscle origin of a muscle. The brace assembly also includes a muscle-insertion portion configured to connect proximate to a muscle insertion of the muscle. The apparatus also includes a force-application assembly. The force-application assembly is configured to connect to the muscle-origin portion and the muscle-insertion portion. The force-application assembly is also configured to extend between the muscle-origin portion and the muscle-insertion portion once coupled to do just so.

In order to mitigate, at least in part, the problems identified above, in accordance with another aspect of my work, I (the inventor) have developed a method. The method includes connecting a muscle-origin portion of a brace assembly proximate to a muscle origin of a muscle. The method also includes connecting a muscle-insertion portion of the brace assembly proximate to a muscle insertion of the muscle. The method also includes connecting a force-application assembly to the muscle-origin portion and to the muscle-insertion portion. The method also includes extending the force-application assembly between the muscle-origin portion and the muscle-insertion portion.

In order to mitigate, at least in part, the problems identified above, in accordance with an aspect of my work, I (the inventor) have developed and provided other aspects as provided in the claims, and/or in the specification.

Other aspects and features of the non-limiting embodiments may now become apparent to those skilled in the art upon review of the following detailed description of the non-limiting embodiments with the accompanying drawings.

BRIEF DESCRIPTION OF DRAWINGS

The non-limiting embodiments may be more fully appreciated by reference to the following detailed description of the non-limiting embodiments when taken in conjunction with the accompanying drawings, in which:

FIGS. 2A, 2B and 2C (SHEET 2 of 10 SHEETS) depict side views of the apparatus of FIG. 1;

FIGS. 7E, 7F and 7G (SHEETS 9 and 10 of 10 SHEETS) depict views of an embodiment of the apparatus 100 of FIG. 1.

Figure 1:
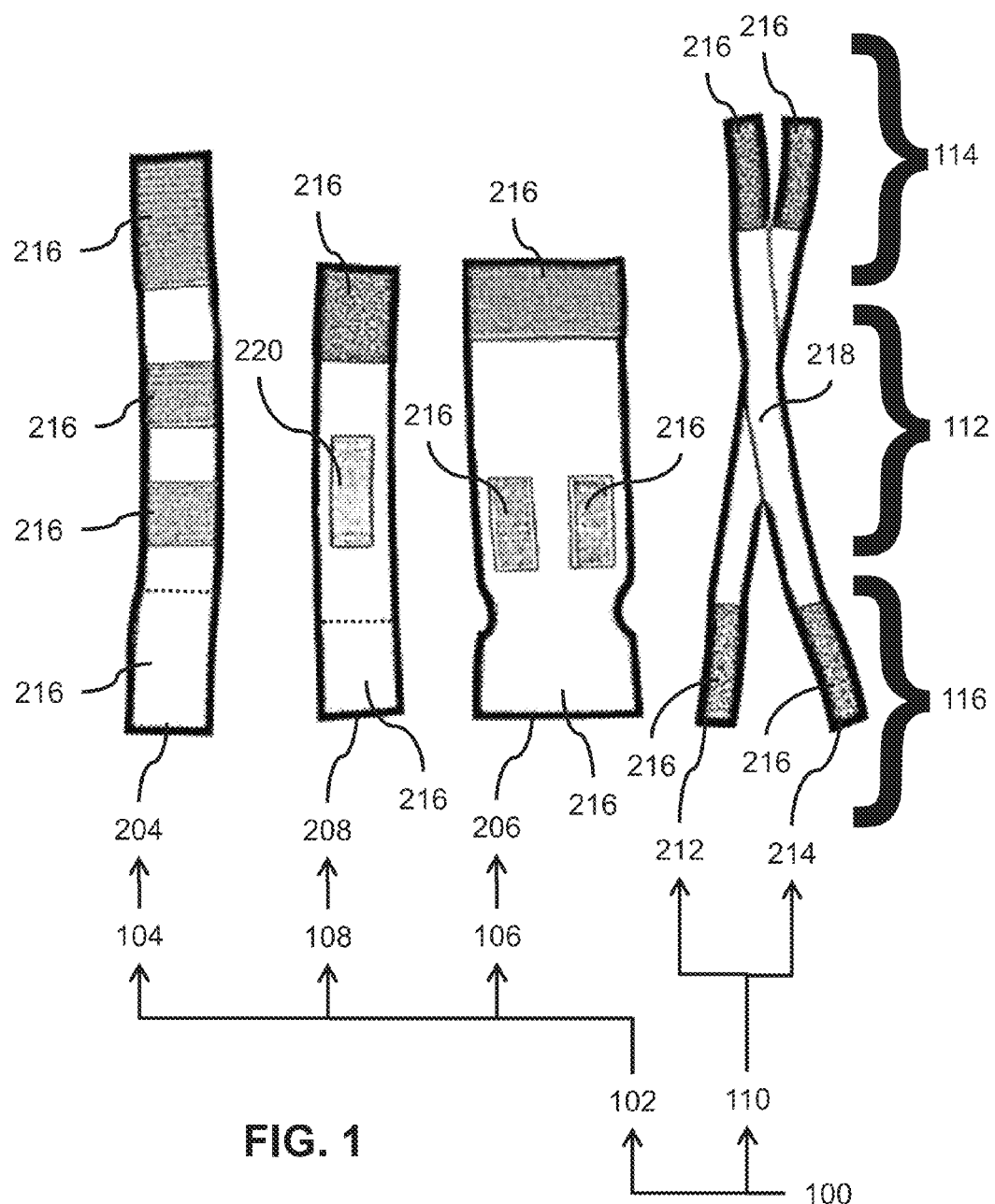
FIG. 1 (SHEET 1 of 10 SHEETS) depicts a top view of an embodiment of an apparatus.

The drawings are not necessarily to scale and may be illustrated by phantom lines, diagrammatic representations and fragmentary views. In certain instances, details not necessary for an understanding of the embodiments (and/or details that render other details difficult to perceive) may have been omitted.

Corresponding reference characters indicate corresponding components throughout the several figures of the Drawings. Elements in the several figures are illustrated for simplicity and clarity and have not necessarily been drawn to scale. For instance, the dimensions of some of the elements in the figures may be emphasized relative to other elements for facilitating understanding of the various presently disclosed embodiments. In addition, common, but well-understood, elements that are useful or necessary in commercially feasible embodiments are often not depicted in order to facilitate a less obstructed view of the various embodiments of the present disclosure.

LISTING OF REFERENCE NUMERALS USED IN THE DRAWINGS

2 ctibia
4 fibula
6 knee
10 ankle
12 foot
14 calf
100 apparatus
102 brace assembly
104 muscle-origin portion
106 muscle-insertion portion
108 intermediate portion
110 force-application assembly
112 central region
114 first end region
116 second end region
204 upper-calf brace assembly
204*a* upper-calf brace assembly
206 foot-brace assembly
206*a* foot-brace assembly
206*b* foot-brace assembly
208 lower-calf brace assembly
208*a* lower-calf brace assembly
212 first member
214 second member
216 connector
216*a* connector
216*f* second connector
216*m* first connector
218 connection
220 loop connector
300 tibialis anterior muscle
302 tibialis posterior muscle
304 peroneus tertius muscle
306 peroneus longus muscle
308 peroneus brevis muscle
310 muscle origin
312 muscle insertion
500 muscular-activation force
700 foam layer

DETAILED DESCRIPTION OF THE NON-LIMITING EMBODIMENT(S)

The following detailed description is merely exemplary in nature and is not intended to limit the described embodiments or the application and uses of the described embodiments. As used herein, the word "exemplary" or "illustrative" or "embodiment" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of the description herein, the terms "upper," "lower," "left," "rear," "right," "front," "vertical," "horizontal," and derivatives thereof shall relate to the embodiments as oriented in the drawings. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments (examples), aspects and/or concepts defined in the appended claims. Hence, specific dimensions and other physical characteristics relating to the embodiments disclosed herein are not to be considered as limiting, unless the claims expressly state otherwise. It is understood that "at least one" is equivalent to "a".

FIG. 1 depicts a top view of an embodiment of an apparatus 100. In general terms, the apparatus 100 includes a brace assembly 102. The brace assembly 102 includes a muscle-origin portion 104 configured to connect proximate to a muscle origin 310 (depicted in FIG. 4B, FIG. 5, FIG. 6) of a muscle. Specifically, the muscle-origin portion 104 is to be placed over or located proximate to the outer surface (the skin) of the user located proximate to the muscle origin 310.

The brace assembly 102 also includes a muscle-insertion portion 106 configured to connect proximate to a muscle insertion 312 (depicted in FIG. 4B, FIG. 5, FIG. 6) of the muscle. Specifically, the muscle-insertion portion 106 is to be placed over or located proximate to the outer surface (the skin) of the user located proximate to the muscle insertion 312.

The apparatus 100 also includes a force-application assembly 110. The force-application assembly 110 is configured to connect to the muscle-origin portion 104 and the muscle-insertion portion 106. The force-application assembly 110 is also configured to extend between the muscle-origin portion 104 and the muscle-insertion portion 106 once coupled to do just so.

In accordance with a specific embodiment (and not limited thereto), the force-application assembly 110 has a first end region 114, a second end region 116, and a central region 112 configured to extend between the first end region 114 and the second end region 116. The first end region 114 is configured to couple to the muscle-origin portion 104. The second end region 116 is configured to couple to the muscle-insertion portion 106.

It will be appreciated that the apparatus 100 may be applied or used with a muscle associate with the body of the wearer of the apparatus 100, such as the calf muscles of the wearer of the apparatus 100. The apparatus 100 offers improved protection to a joint (associated with the muscle). The apparatus 100 offers improved functionality of the joint. The apparatus 100 offers improved operation and/or function of an appendage of the wearer (user of the apparatus 100). More specifically, the apparatus 100 offers improved operation and/or function of the foot (for instance), especially for the case where reconstruction of the arch of the foot may be achieved by activating the muscles associated with the foot. The activation of the muscles is produce by the apparatus 100 by mimicking the muscular action of a functioning muscle and the direction of the muscle contraction, therefore retraining the memory of the muscle (undergoing therapeutic treatment by using the apparatus 100), in such a way that the muscle may begin to improve proper functionality. The apparatus 100 may provide support on the proximal and the distal tibio-fibular joints by mimicking (at least in part) the action of the ligaments at the joints. The apparatus 100 provides a retraining effect on the muscular system since the apparatus 100 may be used while the user (wearer) performs a routine physical activity (such as walking) The apparatus 100 has been tested using functional neurological testing (muscle testing) with satisfactory results.

In view of the foregoing, it will be appreciated that the user may apply a method associated with the apparatus 100. The method includes connecting a muscle-origin portion 104 of a brace assembly 102 proximate to a muscle origin 310 of a muscle. The method also includes connecting a muscle-insertion portion 106 of the brace assembly 102 proximate to a muscle insertion 312 of the muscle. The method also includes connecting a force-application assembly 110 to the muscle-origin portion 104 and to the muscle-insertion portion 106. The method also includes extending the force-application assembly 110 between the muscle-origin portion 104 and the muscle-insertion portion 106.

The brace assembly 102 includes a muscle-origin portion 104 associated with a muscle origin 310 of a muscle. FIG. 6 depicts various embodiments of muscle origins 310 associated with various muscles that may use the apparatus 100. The muscle-origin portion 104 is configured to be: (A) fixedly connectable proximate to the muscle origin 310 of the muscle, and (B) disconnectable or removable (once no longer needed) from the muscle origin 310 of the muscle. By way of an embodiment, the muscle-origin portion 104 is configured to be wrapped around an appendage (such as the calf) of the user (as depicted in the embodiment of FIG. 5).

According to an embodiment, the muscle-origin portion 104 includes instances of a connector 216 located at opposite ends of the muscle-origin portion 104, and also located midway between the opposite ends of the muscle-origin portion 104. The connector 216 may be adjustable or non-adjustable. By way of an embodiment, instances of the connector 216 may include hook-and-loop connectors, as those found in a VELCRO™ connector (which is an embodiment of an adjustable connector).

Figure 5:
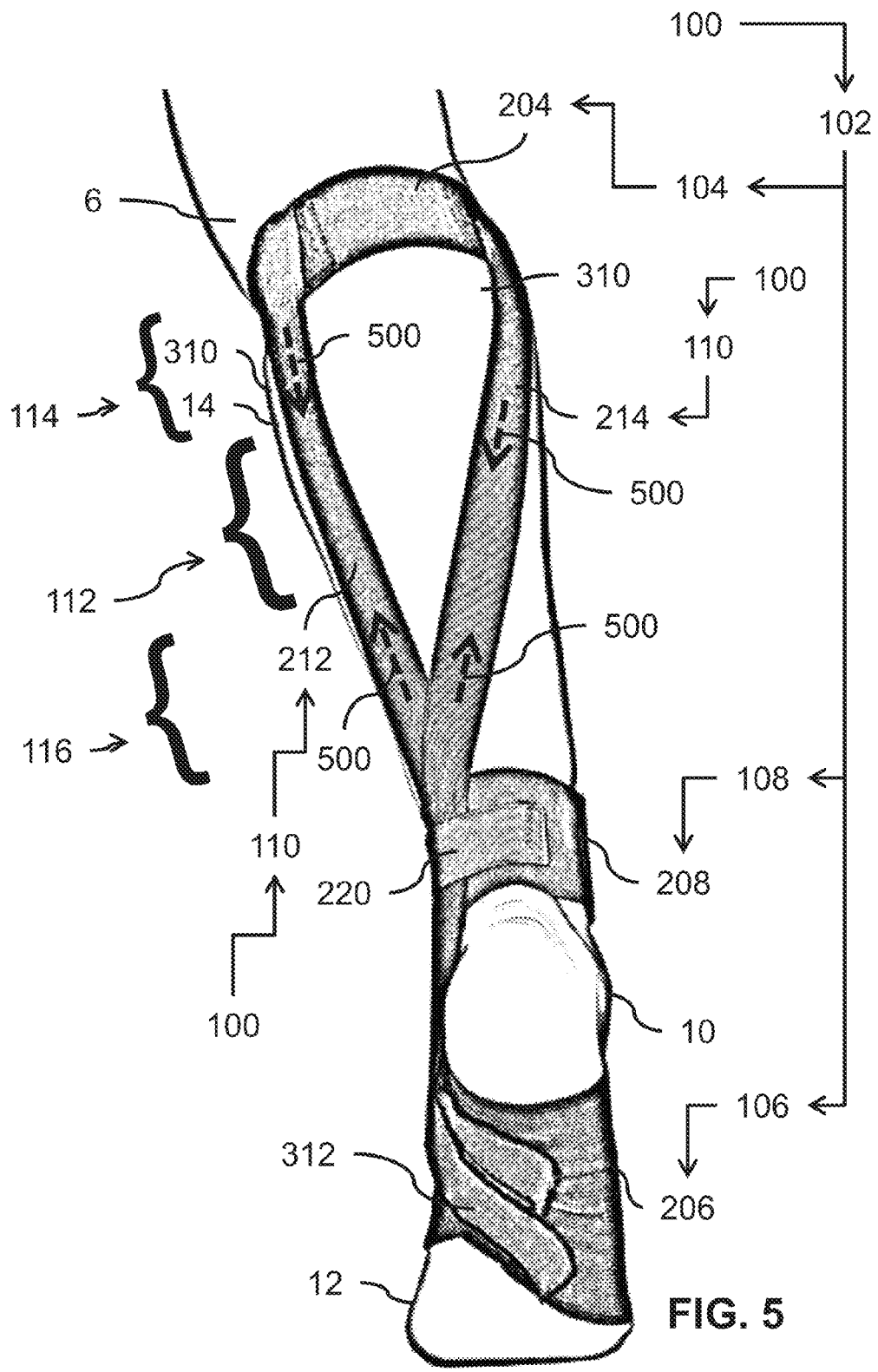
FIG. 5 (SHEET 5 of 10 SHEETS) depicts a posterior view of an embodiment of the apparatus of FIG. 1.
Figure 6:
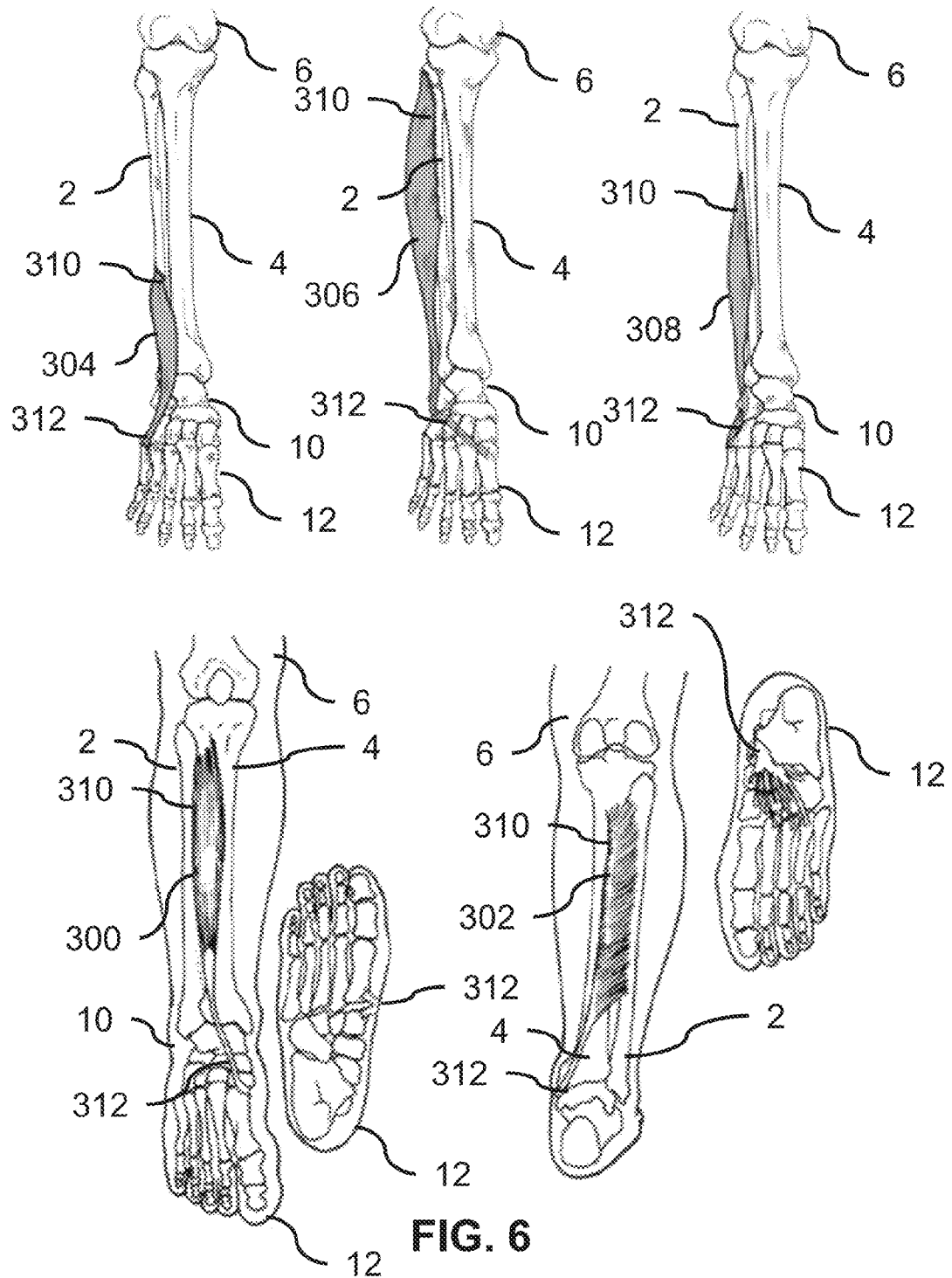
FIG. 6 (SHEET 6 of 10 SHEETS) depicts views of muscles that may receive muscular activation by way of the apparatus of FIG. 1.

According to an embodiment, the muscle-origin portion 104 is configured to be wrapped around the appendage of the user (as depicted in FIG. 5). For this case, the instances of the connector 216 (located at the opposite ends of the muscle-origin portion 104) are configured to fixedly couple with each other once the muscle-origin portion 104 is positioned or placed on the wearer (user).

According to a variation, the muscle-origin portion 104 includes a flexible tubular member. For this case, the end sections of the muscle-origin portion 104 are sewn together by way of stitching (an embodiment of a non-adjustable connector). The tube may be configured to be slid on and off the appendage of the user while remaining substantially in place on the muscle origin 310 (as depicted in FIG. 6) once placed to do just so. The flexible tubular member may be made of neoprene. Neoprene or polychloroprene is a family of synthetic rubbers that are produced by polymerization of chloroprene; neoprene exhibits good chemical stability, and maintains flexibility over a wide temperature range. The muscle-origin portion 104 is configurable for attaching (anchoring) directly to an appendage of the wearer's body. It will be appreciated that other structures may be used in conjunction with the muscle-origin portion 104 for positioning the muscle-origin portion 104 proximate to the muscle origin 310 of a selected muscle.

The brace assembly 102 also includes a muscle-insertion portion 106 associated with a muscle insertion 312 (depicted in FIG. 6) of the muscle. FIG. 6 depicts various embodiments of muscle insertions of various muscles that may use the apparatus 100. The muscle-insertion portion 106 is configured to be: (A) fixedly connected proximate to the muscle insertion 312 of the muscle, and (B) disconnectable or removable (once no longer needed) from the muscle insertion 312 of the muscle. By way of an embodiment, the muscle-origin portion 104 may be configured to be wrapped around an appendage (such as the calf) of the user (as depicted in the embodiment of FIG. 5). In accordance with an embodiment, the muscle-insertion portion 106 may be configured to be wrapped around an appendage of the user such as the calf of the user.

For the case where the muscle-insertion portion 106 is wrapped around the appendage of the user (as depicted in FIG. 5), the muscle-insertion portion 106 includes instances of the connector 216 located at opposite ends of the muscle-insertion portion 106, and also located midway between the opposite ends of the muscle-insertion portion 106. The instances of the connector 216 (located at the opposite ends of the muscle-insertion portion 106) may be configured to fixedly couple with each other once the muscle-insertion portion 106 is positioned or placed proximate to the muscle insertion 312 (depicted in FIG. 6) on the wearer (the user of the apparatus 100). The instances of the connector 216 (located at the opposite ends of the muscle-insertion portion 106) may be configured to be disconnectable or removable (once no longer needed by the user) from proximate to the muscle insertion 312. According to a variation, the muscle-insertion portion 106 includes a flexible tubular member having end sections that are fixedly sewn together, and the flexible tubular member may be manually slid on and off the appendage of the user to an appropriate position relative to the muscle insertion 312 of the muscle. The flexible tubular member may be made of neoprene. The muscle-insertion portion 106 is configurable for attaching (anchoring) directly to an appendage of the wearer's body. It will be appreciated that other structures (bands, etc.) may be used to position the muscle-insertion portion 106 as may be required proximate to the muscle insertion 312.

The term proximal (Latin proximus; nearest) describes where an appendage joins (attaches) the body; the term distal (Latin distare; to stand away from) describes an area or a region furthest from the point of attachment to the body. The muscle origin 310 (depicted in FIG. 6) is a point at which the muscle attaches to a bone. The structure that the muscle origin 310 (sometimes just called "origin") is attached to tends to be the more stable bone in the contraction of the muscle. The site of the muscle origin 310 tends to be more proximal and have greater mass than what the other end of the muscle attaches to. The opposite end of the muscle is called the muscle insertion 312 depicted in FIG. 6 (or simply the "insertion"). The area or the region of muscle insertion 312 tends to be more distal, and have less mass than the site of the muscle origin 310. It is the muscle insertion 312 that tends to move while the body part of the muscle origin 310 is stabilized (or remains relatively stable).

Generally speaking, the brace assembly 102 also includes a force-application assembly 110. The force-application assembly 110 has a central region 112 extending from a first end region 114 configured to couple to the muscle-origin portion 104. The central region 112 extends from a second end region 116 configured to couple to the muscle-insertion portion 106. The force-application assembly 110 extends (or is configured to extend) between the muscle-origin portion 104 and the muscle-insertion portion 106 once the apparatus 100 is coupled to do just so. The force-application assembly 110 is also configured to apply a muscular-activation force 500 (depicted in FIG. 5) to the muscle. The muscular-activation force 500 is configured to urge muscular activation (muscular contraction) of the muscle once coupled and activated to do just so. Muscular activation includes causing or urging the muscle to contract (shortening of muscle length or muscle fibers—sometimes called muscle firing). The muscular-activation force 500 is configured to retrain, at least in part, the muscle. This is done in such a way that the muscle may fire or become activated (as a result of the application of the muscular-activation force 500 to the muscle).

According to an embodiment, the force-application assembly 110 includes instances of the connector 216 located at opposite ends of the force-application assembly 110. An instance of the connector 216 located at a first end of the force-application assembly 110 is configured to fixedly couple with the instance of the connector 216 located in a mid-section (or section) of the muscle-origin portion 104. An instance of the connector 216 located at a second end of the force-application assembly 110 is configured to fixedly couple with the instance of the connector 216 located in a mid-section (or section) of the muscle-insertion portion 106.

In accordance with an embodiment, the force-application assembly 110 may include an elastic member (an elastically deformable member) that remains unattached to the user for a length of the elastic member, in which the length is located between the end sections of the force-application assembly 110. The force-application assembly 110 provides or defines a region of elastomeric activity and creates a spring force. The force-application assembly 110 may include a variety of materials and shapes configured to provide or to apply the muscular-activation force 500. The force-application assembly 110 is configured to resiliently deform during movements of the muscle. The force-application assembly 110 may include at least one elastic material, such as a spring, a bungee, a rubber band, an elastic cord, an elastic panel, an elastic thread, and/or an elongated resistance band, elastic material, an activation device and/or an actuator. The amount or magnitude of the activation force may be controlled depending on the requirements of the user.

According to an embodiment, the brace assembly 102 further includes an intermediate portion 108 positionable between the muscle-origin portion 104 and the muscle-insertion portion 106 on the wearer or the user. The intermediate portion 108 is configured to be fixedly positioned or placed to the wearer (user) either directly or indirectly by way of other suitably arranged structures.

The force-application assembly 110 is configured to slidably couple with the intermediate portion 108 via a loop connector 220. The loop connector 220 is connected to the intermediate portion 108 between the opposite ends of the intermediate portion 108. The loop connector 220 permits confined sliding movement of the force-application assembly 110 (so that the force-application assembly 110 does not flop around but may remain somewhat in a controlled position). For the case where the intermediate portion 108 is configured to wrap around the appendage of the user, the intermediate portion 108 includes instances of the connector 216 (located at opposite ends of the intermediate portion 108). The instances of the connector 216 located at the opposite ends of the intermediate portion 108 may be configured to fixedly couple with each other once the intermediate portion 108 is positioned or placed on the wearer (user), so as to keep the intermediate portion 108 in a fixed location between the muscle-origin portion 104 and the muscle-insertion portion 106. According to a variation, the intermediate portion 108 includes a flexible tubular member (made of neoprene). The intermediate portion 108 is formed as a flexible tubular member having end sections fixedly sewn together, and the flexible tubular member may be slid on and off the appendage of the user.

In accordance with an embodiment, and not limited thereto, the apparatus 100 may be used or may be installed to a calf 14 of the wearer (not shown in FIG. 1 but shown in other FIGS., such as in FIG. 5). The apparatus 100 may be used for treating the muscle, such as including any one of the peroneus longus muscle 306, the peroneus brevis muscle 308, the peroneus tertius muscle 304, the tibialis anterior muscle 300, and/or the tibialis posterior muscle 302 (all depicted in FIG. 6, in which the apparatus 100 is installed or mounted to the calf of the user).

The case where the apparatus 100 is installed to the calf 14 is depicted in FIGS. 2A, 2B, 2C, 3, 4A, 4B, and 5. For this case, the muscle-origin portion 104 includes an upper-calf brace assembly 204 configured to be coupled proximate to a muscle origin 310 (depicted in FIG. 6) of the calf muscle of the calf 14 (see FIG. 5) of the user. The muscle-insertion portion 106 includes a foot-brace assembly 206 configured to be coupled proximate to a muscle insertion 312 (depicted in FIG. 6) of the calf muscle of the user. The force-application assembly 110 includes a first member 212 and a second member 214, which may be connected together by way of a connection 218 at a mid-section of the intermediate portion 108.

FIGS. 2A, 2B and 2C depict side views of the apparatus 100 of FIG. 1 installed to a user (the wearer of the apparatus 100). The user may sit on the floor or a chair in order to install the components of the apparatus 100.

Referring to FIG. 2A, the foot-brace assembly 206 is installed to the foot 12 of the user (in a loop fashion, wrapped around, at least in part, the appendage of the user) so that the foot-brace assembly 206 is positioned proximate to the muscle insertion 312 (depicted in FIG. 6) of any of the muscles depicted in FIG. 6. One end of the first member 212 is coupled to the connector 216 of the foot-brace assembly 206 that is positioned under the foot 12 proximate to the muscle insertion 312.

In accordance with an embodiment, the intermediate portion 108 includes the lower-calf brace assembly 208. The lower-calf brace assembly 208 is installed to the lower calf section of the user (in a loop fashion, wrapped around the appendage or lower calf, of the user). The first member 212 is slid through the loop connector 220 of the lower-calf brace assembly 208. The force-application assembly 110 (provided as the first member 212) is configured to slidably couple with the lower-calf brace assembly 208 (at the loop connector 220). The foot-brace assembly 206 may be called a foot anchor assembly. The foot-brace assembly 206 is configured to be removably securely positioned to the foot (of the user) extending from the leg of the user (on the same leg that the upper-calf brace assembly 204 is positioned). The foot-brace assembly 206 is also configured to support the ligaments located in the foot 12 of the user (while the foot-brace assembly 206 is positioned on the foot 12 to do just so). One end of the second member 214 is coupled to another instance of the connector 216 of the foot-brace assembly 206 that is positioned under the foot 12. The second member 214 is slid through the loop connector 220 of the lower-calf brace assembly 208.

Referring to FIG. 2B, the upper-calf brace assembly 204 is installed to the upper section of the calf 14 of the user below the knee 6 (in a loop fashion, wrapped around the appendage of the user).

Referring to FIG. 2C, the second member 214 is positioned behind the first member 212; the ends of the first member 212 and of the second member 214 are coupled to the upper-calf brace assembly 204. The force-application assembly 110 extends from a fixed connection with the upper-calf brace assembly 204 (past the lower-calf brace assembly 208 in slide coupled arrangement therewith) to a fixed connection with the foot-brace assembly 206. The force-application assembly 110 is (detachably) removably coupled to the upper-calf brace assembly 204. The force-application assembly 110 is (detachably) removably coupled to the foot-brace assembly 206. The force-application assembly 110 is slidably coupled to the lower-calf brace assembly 208. As depicted, the apparatus 100 is configured to provide protection for the ankle joint, elevate the arch of the foot 12, and restore the arch position on the foot 12 (so that the user may walk with adequate support to the foot and the ankle and the knee).

In accordance with the embodiments depicted in FIGS. 2A, 2B and 2C, the upper-calf brace assembly 204 is configured to be securely coupled to the upper portion of the calf 14 of the user proximate to the knee 6 of the user. The lower-calf brace assembly 208 is configured to be securely coupled to the lower portion of the calf 14 of the user proximate to the ankle 10 of the user. The lower-calf brace assembly 208 is spaced apart from the upper-calf brace assembly 204 once the lower-calf brace assembly 208 is securely coupled to the lower portion of the calf 14, and once the upper-calf brace assembly 204 is securely coupled to the upper portion of the calf 14. The foot-brace assembly 206 is configured to be securely coupled to the foot 12 of the user proximate to the ankle 10 of the user. The foot-brace assembly 206 is spaced apart from the lower-calf brace assembly 208 once the foot-brace assembly 206 is securely coupled to the foot 12 of the user, and once the lower-calf brace assembly 208 is securely coupled to the lower portion of the calf 14.

With reference to FIG. 2C, the force-application assembly 110 is further configured to apply the muscular-activation force 500 (depicted in FIG. 5) to the muscle (once coupled and activated to do just so). The muscular-activation force 500 is configured to retrain, at least in part, the muscle associated with (the calf 14 of) the user once the force-application assembly 110 is fixedly coupled to the upper-calf brace assembly 204, passes by the lower-calf brace assembly 208, and is fixedly coupled to the foot-brace assembly 206, and the user begins to walk.

Figure 3:
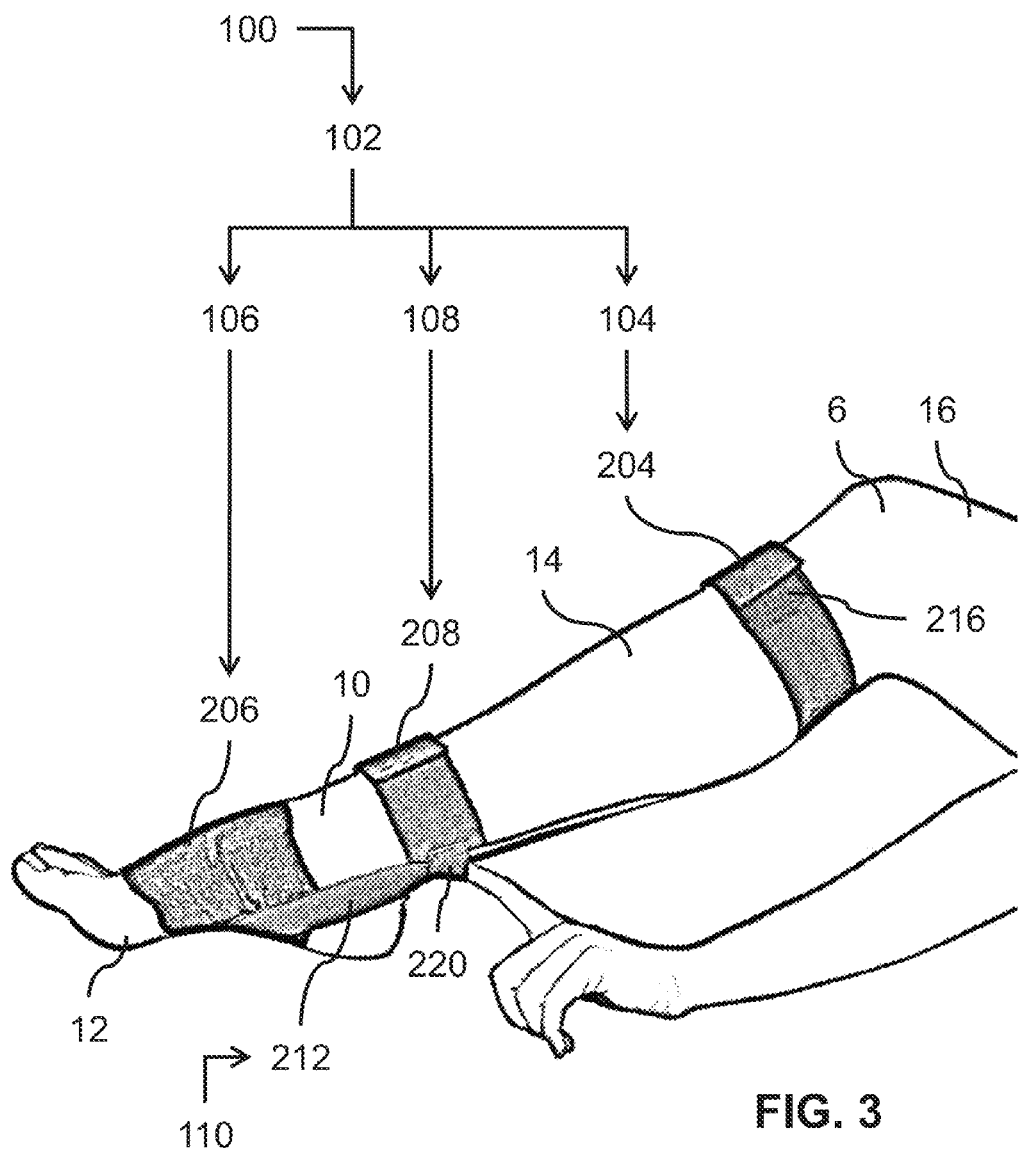
FIG. 3 (SHEET 3 of 10 SHEETS) depicts a side view of an embodiment of the apparatus of FIG. 1.

FIG. 3 depicts a side view of an embodiment of the apparatus 100 of FIG. 1 installed to a user (wearer). The finger of the user extends the loop connector 220 from the lower-calf brace assembly 208 so as to ease slippage of the force-application assembly 110 (such as the first member 212 and the second member 214) through the loop connector 220. The second member 214 is positioned behind the first member 212 (and is thus hidden from view). The loop connector 220 includes a flexible and resilient material having end sections connected to the intermediate portion 108 (or the lower-calf brace assembly 208).

Figure 4:
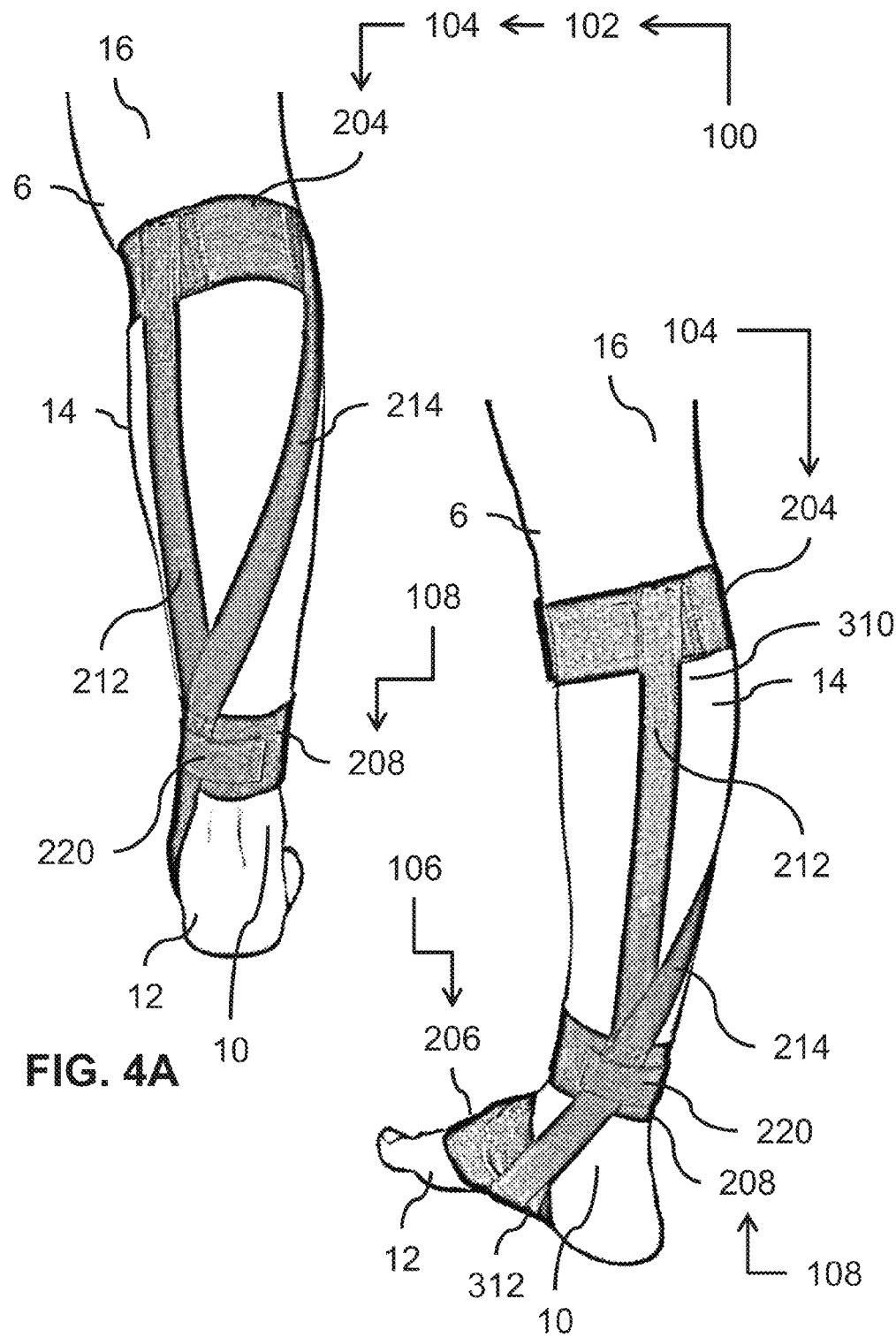
FIGS. 4A and 4B (SHEET 3 of 10 SHEETS) depict posterior views of embodiments of the apparatus of FIG. 1.

FIGS. 4A and 4B depict posterior views of embodiments of the apparatus 100 of FIG. 1 installed to a user (wearer). The wearer is standing.

The brace assembly 102 provides the upper-calf brace assembly 204 configured to be removably securely positioned proximate to the knee joint of the knee 6 of the user. The upper-calf brace assembly 204 is (also known as a knee-anchor assembly. The upper-calf brace assembly 204 is also configured to support the ligaments located at the knee joint of the knee 6 (the proximal tibia-fibula joint).

The brace assembly 102 provides the lower-calf brace assembly 208 configured to be removably securely positioned proximate to the ankle joint of the ankle 10 of the user (on the same leg that the upper-calf brace assembly 204 is positioned, either directly or indirectly). The lower-calf brace assembly 208 may also be called an ankle-anchor assembly. The lower-calf brace assembly 208 is also configured to support the ligaments located at the ankle joint (the distal tibia-fibula joint) of the ankle 10 of the user.

FIG. 5 depicts a posterior view of an embodiment of the apparatus 100 of FIG. 1 installed to a user (wearer).

In accordance with the embodiment of FIG. 5, the force-application assembly 110 is configured to direct the muscular-activation force 500 from the muscle-origin portion 104 and from the muscle-insertion portion 106 along the force-application assembly 110 toward the central region 112 of the force-application assembly 110.

In accordance with an embodiment, the force-application assembly 110 includes the first member 212 extending between the upper-calf brace assembly 204 and the foot-brace assembly 206. The first member 212 terminates at a posterior section of the upper-calf brace assembly 204. The force-application assembly 110 also includes a second member 214 extending between the upper-calf brace assembly 204 and the foot-brace assembly 206. The second member 214 terminates at a lateral section of the upper-calf brace assembly 204. The lateral section is spaced apart from the posterior section.

In accordance with an embodiment, the force-application assembly 110 includes an elastically deformable member.

In accordance with the embodiment of FIG. 5, the force-application assembly 110 is configured to couple to the upper-calf brace assembly 204. The force-application assembly 110 is also configured to couple to the foot-brace assembly 206. The force-application assembly 110 is also configured to apply the muscular-activation force 500 directed from the upper-calf brace assembly 204 and from the foot-brace assembly 206 along the force-application assembly 110 toward a central portion of the force-application assembly 110.

The force-application assembly 110 is configured to retrain the muscle(s) (embodiments of the muscle are depicted in FIG. 6) including any one of the peroneus longus muscle 306, the peroneus brevis muscle 308, the peroneus tertius muscle 304, the tibialis anterior muscle 300, and the tibialis posterior muscle 302 (in any combination and/or permutation thereof). The force-application assembly 110 is configured to mimic (at least in part) the action of a functioning muscle. The force-application assembly 110 is also configured to retrain the memory of the muscle (undergoing treatment) so that the muscle may function properly. The force-application assembly 110 is configured to fire up most of the muscle fibers of the muscle (undergoing treatment). The force-application assembly 110 is configured to urge the muscle (undergoing treatment) to contract (fire or activate) properly so that once the muscle contracts (repeatedly) properly, the operation of the muscle protects the joints (at the knee 6 and the ankle 10). For the case where a muscle functions properly, at least 80% or more of the muscle fibers fire (operate) in a synchronism, what may be called a summation of the muscle fibers (a summation contraction of the muscle fibers). For the case where the muscle is not functioning properly (not firing properly), the muscle operates from 20% to 50% of muscle functionality. The brace assembly 102 is configured to provide support on the tibia-fibula joint, proximal and distal, at the knee 6 and at the ankle 10.

The brace assembly 102 is configured to increase the function of the muscle from a range of about 20% to about 50% of muscle function to about 80% or higher. The brace assembly 102 improves, at least in part, muscle function, protection of the joints, functionality of the joint, and operation/function of the foot 12 (especially in the case where reconstruction of the arch of the foot is achieved by activating the muscle or muscles).

The brace assembly 102 is a retraining mechanism configured to overcome injuries, trauma, and wear and tear for people that run a lot by retraining the muscle(s) by way of muscle activation.

The brace assembly 102 is used in a progressive manner by the user. Initially, for 30 minutes to start, and then the user may build up to an hour or two hours of use a day, depending on the nature and/or impact of the injury or the nature of the problem the user is experiencing. The brace assembly 102 is to be installed to the user as described above, and then used by the user (for instance) while walking using the walking gait. The brace assembly 102 has a retraining effect on the muscular system because the user is retraining while the user is performing a physical activity, in this case, walking The brace assembly 102 provides a mechanism for retraining the muscle (by way of muscle activation) into muscle flexion and muscle extension within the regular action function of the user (for instance, while walking) The apparatus 100 was not intended to the used by the user positioned in a reclined position sitting in a chair and flexing the ankle 10 back and forth, or moving a leg around; the apparatus 100 is meant to be used (for best results) while walking (or performing other mobile functional duties). However, there is some benefit for wearing the apparatus 100 during the day because the apparatus 100 provides a constant pull (muscular activation) while the user is in motion, thus leading to a retraining and resetting of the muscle, and thus the apparatus 100 acts like a dynamic brace.

The upper-calf brace assembly 204 and the lower-calf brace assembly 208 are each configured to treat a variety of lower leg injuries, including knee injuries, injury as a result of a lateral sprain on the ankles, improper footwear and so on. The knee 6 and the ankle 10 may receive stress injuries or sustain sprained or strained ligaments. The upper-calf brace assembly 204 and the lower-calf brace assembly 208 may provide relief of the strain and mimic the action of the ligament, while the muscle is rebuilding and retraining while the user walks.

FIG. 6 depicts views of muscles that may be activated by using the apparatus 100 of FIG. 1.

Muscle origin 310 and muscle insertion 312 are depicted or indicated for each type of muscle in FIG. 6. The apparatus 100 may be used with the tibialis anterior muscle 300 (the anterior view is on the left side, and the plantar view is on the right side). The apparatus 100 may also be used with the tibialis posterior muscle 302 (posterior view is on the left side, and the plantar view is on the right side). The apparatus 100 may also be used with the peroneus tertius muscle 304. The apparatus 100 may also be used with the peroneus longus muscle 306. The apparatus 100 may also be used with the peroneus brevis muscle 308.

The brace assembly 102 is configured to retrain the peroneal muscles, including the peroneus longus muscle 306, the peroneus brevis muscle 308, and the peroneus tertius muscle 304; these muscles follow the line of the fibula 4 on the lateral side of the fibula 4. The peroneus longus muscle 306 turns the sole of the foot outward. It is a long, strap-like muscle located on the outside of the lower leg. It connects the tibia 2 (depicted in FIG. 6) and the fibula 4 (depicted in FIG. 6) to the foot by means of a stout tendon that passes behind the lateral malleolus (network of nerves and muscles around the ankle 10). It functions in eversion of the foot, assists in plantar flexion (moving it downward), and helps support the arch of the foot.

The tibia 2 is also known as the shinbone or shank bone, is the larger and stronger of the two bones in the leg below the knee 6 in vertebrates (the other being the fibula 4), and it connects the knee 6 with the ankle bones. The tibia 2 is found next to the fibula 4 on the medial side of the leg, closer to centre-line. The fibula 4 (calf bone) is a leg bone located on the lateral side of the tibia 2, with which it is connected above and below. It is the smaller of the two bones, and, in proportion to its length, the slenderest of all the long bones.

Figure 7A:
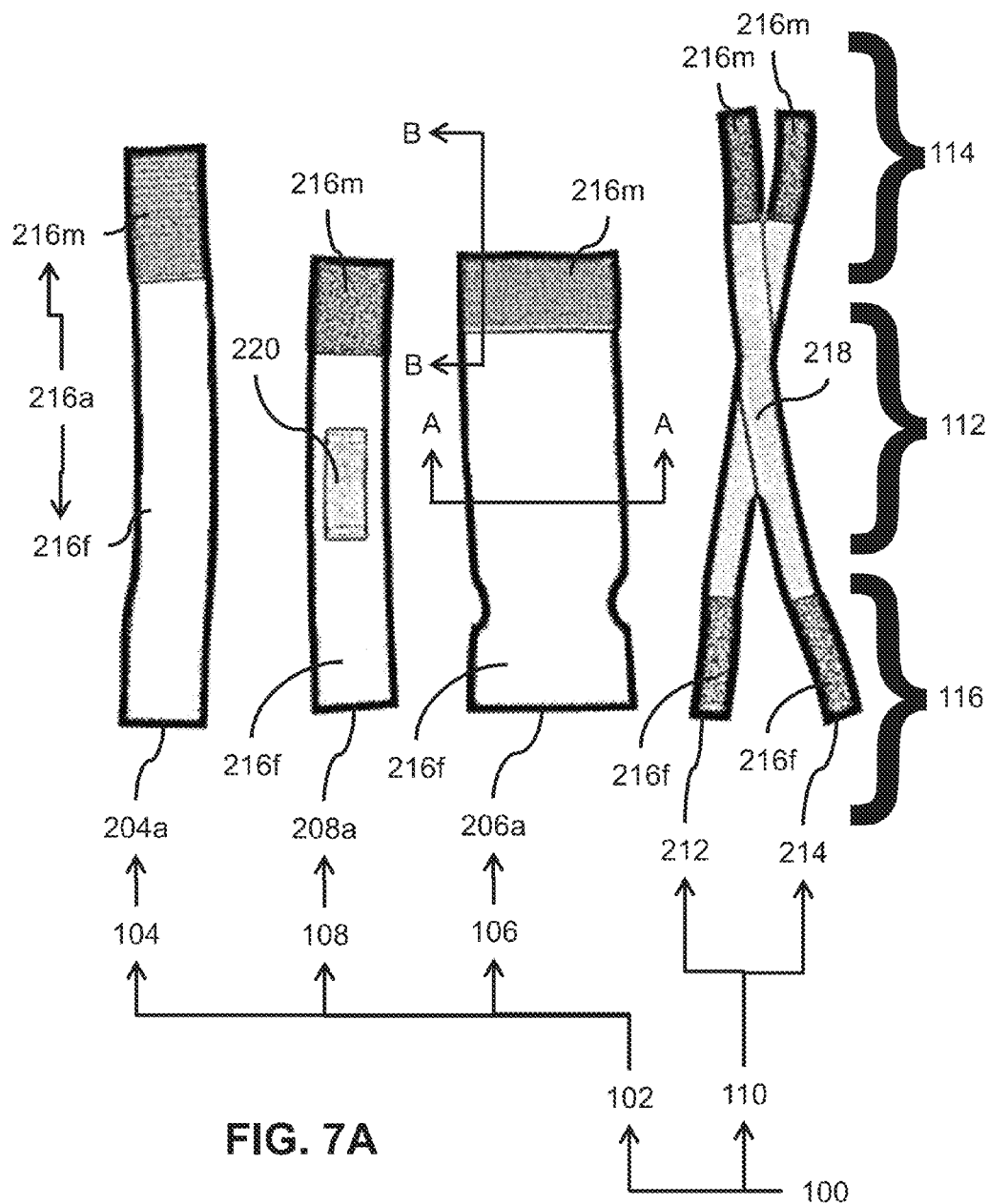
FIG. 7A (SHEET 7 of 10 SHEETS) depicts a view of an embodiment of the apparatus 100 of FIG. 1.

FIG. 7A depicts a view of an embodiment of the apparatus 100 of FIG. 1.

FIG. 7A depicts a top view of an embodiment of the apparatus 100 of FIG. 1, in which modifications have been made. The loop connector 220, the first member 212 and the second member 214 (each depicted in FIG. 1) do not change for the embodiment depicted in FIG. 7A. The first member 212 and the second member 214 include an elastic (resilient) material. The loop connector 220 may or may not include an elastic (resilient) material. The loop connector 220 is configured to be relocatable or repositionable (constructed so as to be movable) on the second connector 216f of the lower-calf brace assembly 208a. For instance, to accommodate the different sizes of the user's limb, the loop connector 220 may be positioned (repositioned) on the lower-calf brace assembly 208a after the lower-calf brace assembly 208a is positioned fixedly to the skin of the user. In addition, the connection 218 includes a latex-free elastic material.

Figure 7B:
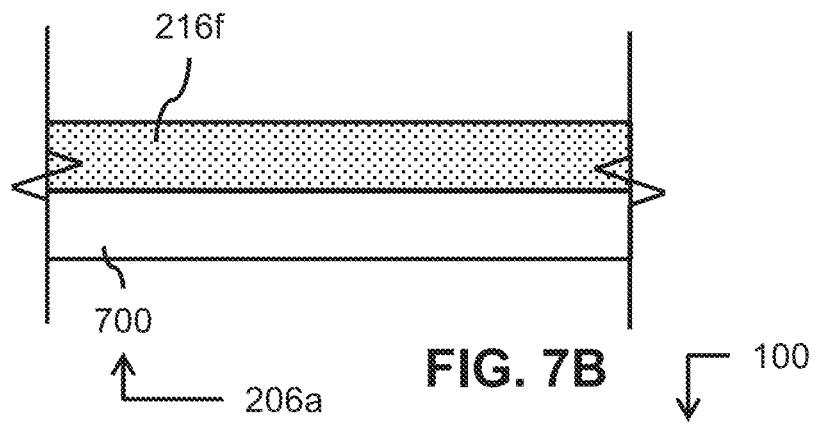
FIGS. 7B, 7C and 7D (SHEET 8 of 10 SHEETS) depict views of embodiments of the apparatus 100 of FIG. 1.
Figure 7C:
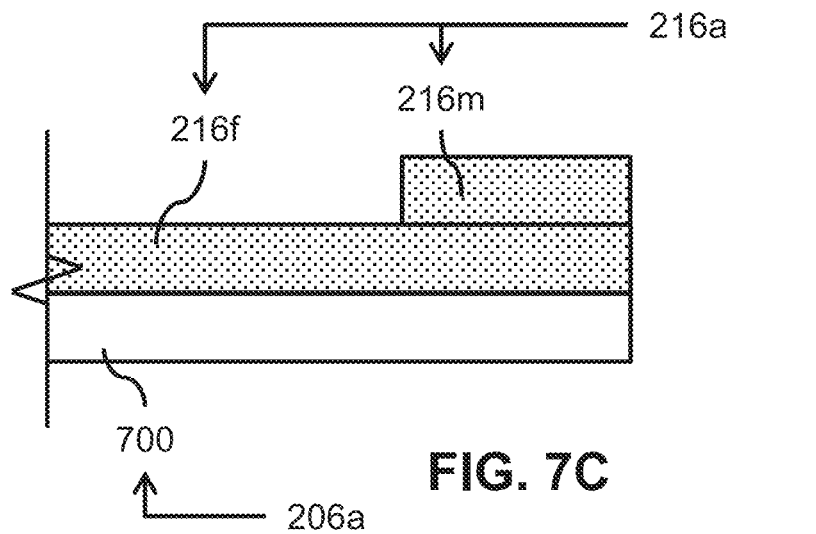
Figure 7D:
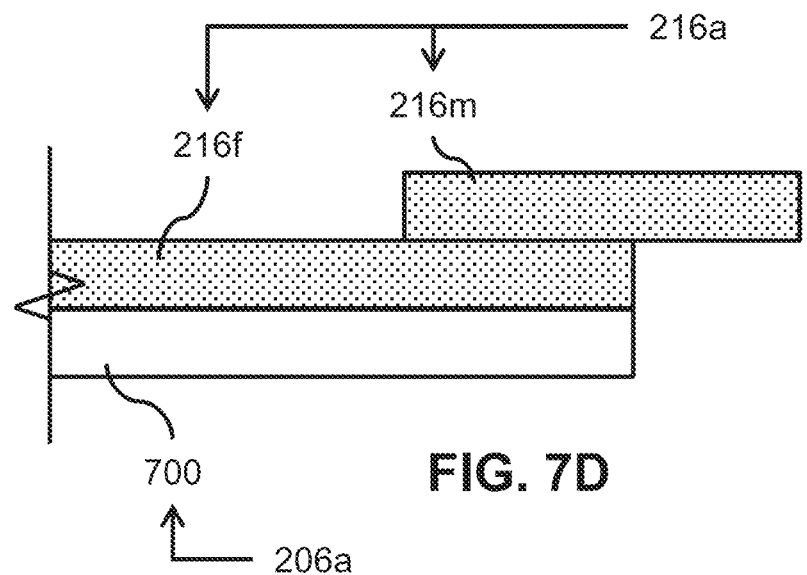

A connector 216a is a modification of the connector 216 (depicted in FIG. 1). The connector 216a (fabric foam) includes a combination of a first connector 216m, a second connector 216f and a foam layer 700. The foam layer 700 is depicted in FIGS. 7B, 7C and 7D.

An upper-calf brace assembly 204a is a modification of the upper-calf brace assembly 204 (depicted in FIG. 1). The upper-calf brace assembly 204a includes a combination of the second connector 216f, the first connector 216m and the foam layer 700 (depicted in FIGS. 7B, 7C and 7D). It will be appreciated that the upper-calf brace assembly 204a may form any suitable shape.

A foot-brace assembly 206a is a modification of the foot-brace assembly 206 (depicted in FIG. 1). The foot-brace assembly 206a includes a combination of the second connector 216f, the first connector 216m and the foam layer 700 (depicted in FIGS. 7B, 7C and 7D). In accordance with FIG. 7A, the foot-brace assembly 206a defines a rectangular shaped outer perimeter. It will be appreciated that the foot-brace assembly 206a may form any suitable shape.

A lower-calf brace assembly 208a is a modification of the lower-calf brace assembly 208 (depicted in FIG. 1). The lower-calf brace assembly 208a includes a combination of the second connector 216f, the first connector 216m and the foam layer 700 (depicted in FIGS. 7B, 7C and 7D). It will be appreciated that the lower-calf brace assembly 208a may form any suitable shape.

The first connector 216m and the second connector 216f are configured to selectively connect with each other. The first connector 216m (also called a male connector) includes a touch fastener element (also called a touch fastener male element). The first connector 216m may include a transparent (translucent) flexible touch fastener (such as, the VELCRO brand fastener having a translucent plastic material). The transparent (translucent) flexible touch fastener is configured to: (A) not attract lint (and seldom snags clothing), and (B) mate with loop and soft strapping materials.

The second connector 216f (also called a female connector) includes a touch fastener element (also called a touch fastener female element). The second connector 216f includes a material (such as, a synthetic breathable material) configured to interact with the material of the first connector 216m. The second connector 216f extends substantially across the length of the connector 216a. The first connector 216m is attached to an end portion of the second connector 216f. Once the foot-brace assembly 206a is wrapped around the foot of the user (the wearer of the apparatus 100), the first connector 216m is positioned to attach to an opposite end portion of the second connector 216f (ad depicted in FIG. 7G).

FIGS. 7B, 7C and 7D depict views of embodiments of the apparatus 100 of FIG. 1.

FIGS. 7B, 7C and 7D depict cross-sectional views of an embodiment of the foot-brace assembly 206a for use with the apparatus 100 of FIG. 1. FIG. 7B depicts a cross-sectional side view of the foot-brace assembly 206a of FIG. 7A taken along the cross-section line A-A (of FIG. 7A). FIG. 7C depicts a cross-sectional side view of the foot-brace assembly 206a of FIG. 7A taken along the cross-section line B-B (of FIG. 7A). FIG. 7D depicts a cross-sectional side view of the foot-brace assembly 206a of FIG. 7A (as an option to the embodiment of FIG. 7C).

It will be appreciated that the description of the foot-brace assembly 206a (depicted in FIGS. 7B, 7C and 7D are applicable to the upper-calf brace assembly 204a and the lower-calf brace assembly 208a of FIG. 7A (if so desired).

The foot-brace assembly 206a includes the second connector 216f bonded to the foam layer 700. The foam layer 700 is configured to touch (make contact with) the skin of the user (the wearer of the apparatus 100 of FIG. 1) once the foam layer 700 is positioned to do just so. The second connector 216f is positioned over, and securely connects to (is bonded to) the foam layer 700. Similarly, the upper-calf brace assembly 204a and the lower-calf brace assembly 208a of FIG. 7A each also includes the second connector 216f bonded to the foam layer 700 (if so desired).

The foot-brace assembly 206a includes a woven composite having a nylon component, a SPANDEX™ component and a foam component (and any equivalent thereof). Spandex™ is an elastic synthetic fiber. The Lycra™ product is an equivalent of the Spandex™ product. Spandex™ includes a polyurethane-polyurea copolymer. The foot-brace assembly 206a is configured to provide a degree of two-directional stretch while allowing for adjustable compression (to be applied to the user's skin) The foot-brace assembly 206a is also configured to provide reasonably rigid support (useful for restricting mobility). The foot-brace assembly 206a is also configured to provide a dermatologically safe material. The foot-brace assembly 206a is also configured to be wrapped on the body (a body portion) of the user. The foot-brace assembly 206a is also configured to be securely positioned on the body of the user (using any suitable connectors, hook and loop connector, touch fastener, etc.).

An embodiment of the foot-brace assembly 206a (the combination of the second connector 216f and the foam layer 700) is provided by any one of: (A) the MediWrap™ product; (B) the ProWrap™ product; (C) the NuStim-Wrap™; and (D) the SuperWrap™ product all manufactured by Fabrifoam™ Products located in Exton, Pa., USA.

Referring to FIG. 7C, the first connector 216m does not extend past a peripheral edge of the second connector 216f. The first connector 216m is fixedly attached to the proximate zone of the peripheral edge of the second connector 216f.

Referring to FIG. 7D, the first connector 216m extends past the peripheral outer edge of the second connector 216f. The first connector 216m is fixedly attached to the proximate zone of the peripheral edge of the second connector 216f.

The apparatus 100 is adapted so that any one of the upper-calf brace assembly 204, the foot-brace assembly 206 and the lower-calf brace assembly 208 includes the connector 216. The connector 216 has the first connector 216m. The connector 216 also has the second connector 216f. The first connector 216m and the second connector 216f are configured to selectively connect with each other. The second connector 216f extends substantially across a length of the connector 216. The first connector 216m is attached to an end portion of the second connector 216f. The connector 216 also has the foam layer 700. The second connector 216f is bonded to the foam layer 700. The foam layer 700 is configured to touch (make contact with) the user once positioned to do just so.

Figure 7G:
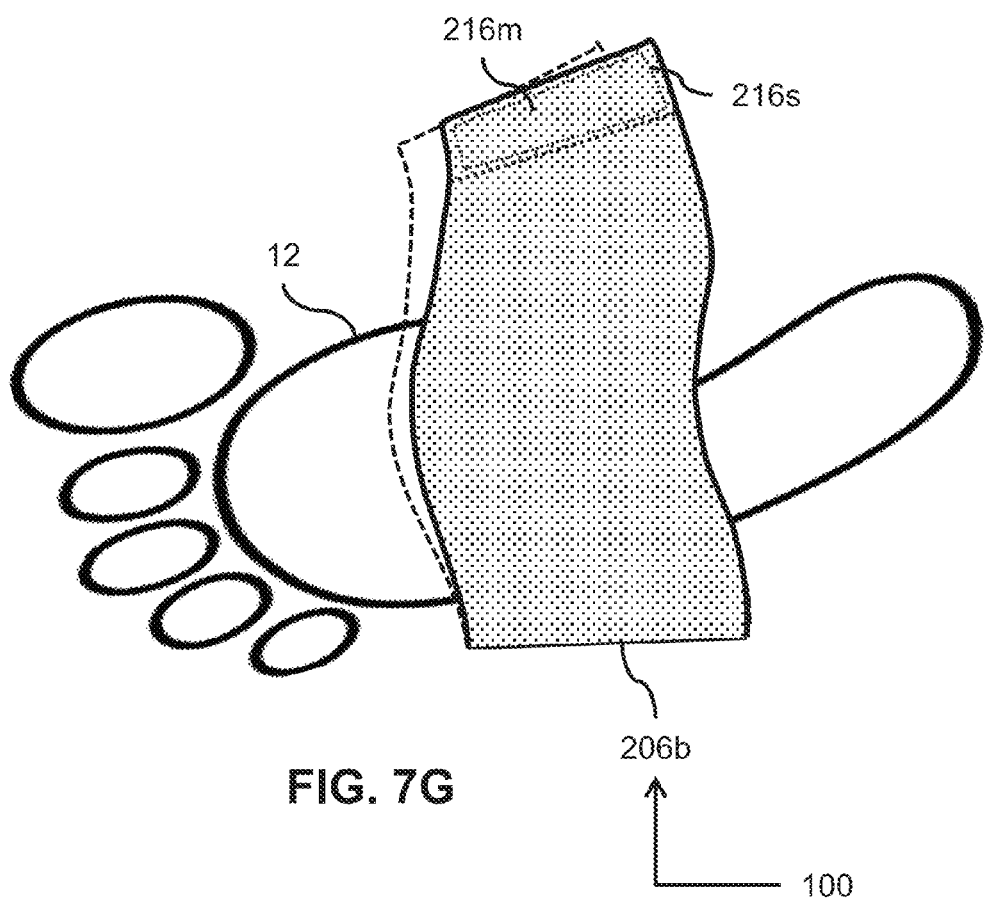

FIGS. 7E, 7F and 7G depict views of an embodiment of the apparatus 100 of FIG. 1.

A foot-brace assembly 206b is a modification of the foot-brace assembly 206 of FIG. 1. Specifically, FIGS. 7E, 7F and 7G depict views of embodiments of the foot-brace assembly 206a for use with the apparatus 100 of FIG. 1. Referring to the embodiments of FIGS. 7E, 7F and 7G, the foot-brace assembly 206a defines a shape configured to ergonomically conform, at least in part, to the mid portion of the foot 12 of the user. FIG. 7E depicts the outer view of the foot-brace assembly 206b in which the second connector 216f is shown (and the foam layer 700 is hidden behind the second connector 216f). FIG. 7F depicts the inner view of the foot-brace assembly 206b in which the foam layer 700 is shown (and the second connector 216f is hidden behind the foam layer 700). The first connector 216m is positioned at one side of the second connector 216f. Once positioned, the stitching 216s is applied in such a way as to securely connect the first connector 216m and the second connector 216f together. Referring to the embodiment of FIG. 7G, the foot-brace assembly 206a is depicted as being folded approximately in half and partially wrapped around the foot 12 of the user (the wearer of the apparatus 100).

It may be appreciated that the assemblies and modules described above may be connected with each other as may be required to perform desired functions and tasks that are within the scope of persons of skill in the art to make such combinations and permutations without having to describe each one of them in explicit terms. There is no particular assembly, or components that are superior to any of the equivalents available to the art. There is no particular mode of practicing the disclosed subject matter that is superior to others, so long as the functions may be performed. It is believed that all the crucial aspects of the disclosed subject matter have been provided in this document. It is understood that the scope of the present invention is limited to the scope provided by the independent claim(s), and it is also understood that the scope of the present invention is not limited to: (i) the dependent claims, (ii) the detailed description of the non-limiting embodiments, (iii) the summary, (iv) the abstract, and/or (v) the description provided outside of this document (that is, outside of the instant application as filed, as prosecuted, and/or as granted). It is understood, for the purposes of this document, that the phrase "includes" is equivalent to the word "comprising." It is noted that the foregoing has outlined the non-limiting embodiments (examples). The description is made for particular non-limiting embodiments (examples). It is understood that the non-limiting embodiments are merely illustrative as examples.

What is claimed is:

1. An apparatus for a user, the apparatus comprising:
   a brace assembly including:
      a muscle-origin portion being configured to connect proximate to a muscle origin of a muscle of the user, and
      a muscle-insertion portion being configured to connect proximate to a muscle insertion of the muscle; and
   a force-application assembly being configured to connect to the muscle-origin portion and the muscle-insertion portion, and extend between the muscle-origin portion and the muscle-insertion portion once coupled to do just so; and
   wherein the muscle of the user includes the tibialis posterior muscle of the calf of the user, in which the tibialis posterior muscle is connected to, and extends between, the muscle insertion and the muscle origin, in which the muscle insertion is located at the medial side of the foot of the user, in which the medial side is positioned opposite from the lateral side of the foot of the user, and in which the muscle origin of the tibialis posterior muscle is located proximate to the rear of, and below, the knee of the user; and
   wherein the muscle-insertion portion includes a foot-brace assembly configured to be coupled to the foot of the user on the medial side of the foot of the user at a position that is located proximate to the muscle insertion of the tibialis posterior muscle; and
   wherein the muscle-origin portion further includes an upper-calf brace assembly configured to be coupled proximate to below the knee of the user at a position that is located proximate to the muscle origin of the tibialis posterior muscle, and the upper-calf brace assembly includes a first section and a second section, in which the second section is spaced apart from the first section; and
   wherein the force-application assembly includes a first elastic member configured to be (A) coupled to the first section of the upper-calf brace assembly, (B) coupled to the foot-brace assembly on the medial side of the foot of the user proximate to the muscle insertion of the tibialis posterior muscle, and (C) unconnected to the lateral side of the foot-brace assembly at the lateral side of the foot of the user, in such a way that the first elastic member, in use, extends between (a) the foot-brace assembly on the medial side of the foot of the user at the position that is located proximate to the muscle insertion of the tibialis posterior muscle, and (b) the first section of the upper-calf brace assembly at the position that is located proximate to the muscle origin of the tibialis posterior muscle; and
   wherein the force-application assembly further includes a second elastic member configured to be (A) coupled to the second section of the upper-calf brace assembly, (B) coupled to the foot-brace assembly on the medial side of the foot of the user proximate to the muscle insertion of the tibialis posterior muscle, and (C) unconnected to the lateral side of the foot-brace assembly at the lateral side of the foot of the user, in such a way that the second elastic member, in use, extends between (a) the foot-brace assembly on the medial side of the foot of the user at the position that is located proximate to the muscle insertion of the tibialis posterior muscle, and (b) the second section of the upper-calf brace assembly at the position that is located proximate to the muscle origin of the tibialis posterior muscle; and
   wherein the first elastic member and the second elastic member of the force-application assembly are configured to, in use, align, at least in part, along the medial side of the foot of the user, and to activate, the tibialis posterior muscle in such a way that the first elastic member and the second elastic member:
  mimic muscular action and contraction of the tibialis posterior muscle; and
  elevate the arch of the foot and restore the arch position of the foot so that the user walks with adequate support to the foot, the ankle and the knee of the user.

2. The apparatus of claim 1, wherein:
the force-application assembly is configured to apply a muscular-activation force urging muscular contraction of the muscle once coupled and activated to do just so.

3. The apparatus of claim 1, wherein:
the force-application assembly is configured to direct a muscular-activation force from the muscle-origin portion and from the muscle-insertion portion along the force-application assembly toward a central region of the force-application assembly.

4. The apparatus of claim 1, wherein:
the force-application assembly is configured to:
  apply a muscular-activation force directed from the upper-calf brace assembly and from the foot-brace assembly along the force-application assembly toward a central portion of the force-application assembly.

5. The apparatus of claim 1, wherein:
the brace assembly further includes an intermediate portion being positionable between the muscle-origin portion and the muscle-insertion portion; and
the force-application assembly is configured to slidably couple with the intermediate portion.

6. The apparatus of claim 5, wherein:
the intermediate portion includes:
  a lower-calf brace assembly; and
  the force-application assembly is configured to slidably couple with the lower-calf brace assembly.

7. The apparatus of claim 6, wherein:
the foot-brace assembly is spaced apart from the lower-calf brace assembly once the foot-brace assembly is securely coupled to a foot of the user, and once the lower-calf brace assembly is securely coupled to a lower portion of a calf of the user.

8. The apparatus of claim 1, wherein:
the force-application assembly is further configured to:
  apply a muscular-activation force, and the muscular-activation force is configured to retrain, at least in part, the muscle.

9. The apparatus of claim 1, wherein:
the brace assembly further includes:
  an intermediate portion having a lower-calf brace assembly configured to be securely coupled to a lower portion of a calf of the user proximate to an ankle of the user.

10. The apparatus of claim 9, wherein:
the lower-calf brace assembly is spaced apart from the upper-calf brace assembly once:
  the lower-calf brace assembly is securely coupled to the lower portion of the calf; and
  the upper-calf brace assembly is securely coupled to an upper portion of the calf.

11. The apparatus of claim 1, wherein:
the force-application assembly is further configured to:
  apply a muscular-activation force, in which the muscular-activation force is configured to retrain, at least in part, the muscle associated with a calf of the user once the force-application assembly is fixedly coupled to the upper-calf brace assembly, passes by a lower-calf brace assembly, and is fixedly coupled to the foot-brace assembly.

12. The apparatus of claim 1, wherein:
the first elastic member extends between the upper-calf brace assembly and the foot-brace assembly, and the first elastic member, in use, terminates at a posterior section of the upper-calf brace assembly; and
the second elastic member extends between the upper-calf brace assembly and the foot-brace assembly, and the second elastic member, in use, terminates at a lateral section of the upper-calf brace assembly, in which the lateral section is spaced apart from the posterior section.

13. The apparatus of claim 1, wherein:
the brace assembly further includes:
  an intermediate portion being positionable between the muscle-origin portion and the muscle-insertion portion; and
the force-application assembly includes:
  an elastically deformable member configured to slidably couple with the intermediate portion.

14. The apparatus of claim 13, wherein:
the first elastic member terminates at a posterior section of the upper-calf brace assembly; and
the second elastic member terminates at a lateral section of the upper-calf brace assembly, in which the lateral section is spaced apart from the posterior section.

15. The apparatus of claim 1, further comprising:
a connector having:
  a first connector;
  a second connector, the first connector and the second connector being configured to selectively connect with each other, the second connector extending substantially across a length of the connector, and the first connector being attached to an end portion of the second connector; and
  a foam layer, the second connector being bonded to the foam layer, and the foam layer being configured to touch the user once positioned to do just so.

* * * * *